(12) United States Patent
Lentz et al.

(10) Patent No.: US 7,004,937 B2
(45) Date of Patent: Feb. 28, 2006

(54) WIRE REINFORCED ARTICULATION SEGMENT

(75) Inventors: David J. Lentz, La Jolla, CA (US); Phillip A. Estepa, San Diego, CA (US)

(73) Assignee: Cryocor, Inc., San Diego, CA (US)

( * ) Notice: Subject to any disclaimer, the term of this patent is extended or adjusted under 35 U.S.C. 154(b) by 570 days.

(21) Appl. No.: 10/210,616

(22) Filed: Jul. 31, 2002

(65) Prior Publication Data

US 2004/0024413 A1 Feb. 5, 2004

(51) Int. Cl.
*A61B 18/18* (2006.01)

(52) U.S. Cl. ...................... 606/22; 604/95.04
(58) Field of Classification Search ............... 606/108, 606/1, 20–26, 129; 604/264, 523–284
See application file for complete search history.

(56) References Cited

U.S. PATENT DOCUMENTS

| | | | |
|---|---|---|---|
| 1,060,665 A | 5/1913 | Bell | |
| 2,574,840 A | 11/1951 | Pieri | |
| 2,688,329 A | 9/1954 | Wallace | |
| 3,605,725 A | 9/1971 | Bentov | |
| 3,696,813 A | 10/1972 | Wallach | |
| 4,245,624 A | 1/1981 | Komiya | |
| 4,456,017 A | 6/1984 | Miles | |
| 4,586,923 A * | 5/1986 | Gould et al. ............. | 604/95.04 |
| 4,757,827 A | 7/1988 | Buchbinder | |
| 4,813,434 A * | 3/1989 | Buchbinder et al. ........ | 600/585 |
| 4,815,478 A | 3/1989 | Buchbinder | |
| 4,886,067 A | 12/1989 | Palermo | |
| 4,960,411 A | 10/1990 | Buchbinder | |
| 5,108,368 A | 4/1992 | Hammerslag et al. | |
| 5,114,414 A | 5/1992 | Buchbinder | |
| 5,125,895 A | 6/1992 | Buchbinder | |
| 5,228,441 A | 7/1993 | Lundquist | |
| 5,275,151 A | 1/1994 | Shockey et al. | |
| 5,318,526 A | 6/1994 | Cohen | |
| 5,322,064 A | 6/1994 | Lundquist | |
| 5,327,906 A | 7/1994 | Fideler | |
| 5,330,466 A | 7/1994 | Imran | |
| 5,334,145 A | 8/1994 | Lundquist et al. | |
| 5,368,564 A | 11/1994 | Savage | |
| 5,383,852 A | 1/1995 | Stevens-Wright | |
| 5,531,686 A * | 7/1996 | Lundquist et al. ....... | 604/95.04 |
| 5,656,030 A | 8/1997 | Hunjan et al. | |
| 5,715,817 A | 2/1998 | Stevens-Wright et al. | |
| 5,813,997 A * | 9/1998 | Imran et al. ................ | 600/585 |
| 5,906,590 A | 5/1999 | Hunjan et al. | |
| 5,944,689 A * | 8/1999 | Houser et al. ........... | 604/95.04 |
| 5,971,975 A * | 10/1999 | Mills et al. ................. | 604/527 |
| 6,013,052 A | 1/2000 | Durman et al. | |

(Continued)

FOREIGN PATENT DOCUMENTS

EP 0737482 A2 10/1996

*Primary Examiner*—Glenn K. Dawson
(74) *Attorney, Agent, or Firm*—Nydegger & Associates

(57) ABSTRACT

A device for steering a cardiac cryoablation catheter through the vasculature of a patient includes separate first and second deflection members that connect a tip member to the distal end of a catheter tube. Importantly, the first deflection member has a first flexural modulus, and the second deflection member has a second flexural modulus that is greater than the first flexural modulus. Also included is a control wire for pulling the tip member toward the catheter tube. In response, the first and second deflection members differentially deflect, according to their respective flexural moduli, to move the tip member for steering the catheter through the vasculature.

18 Claims, 2 Drawing Sheets

U.S. PATENT DOCUMENTS

| | | | |
|---|---|---|---|
| 6,066,125 A | 5/2000 | Webster, Jr. |
| 6,123,699 A | 9/2000 | Webster, Jr. |
| 6,146,378 A | 11/2000 | Mikus et al. |
| 6,149,574 A | 11/2000 | Trauthen |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,267,746 B1 | 7/2001 | Bumbalough |
| 6,270,476 B1 | 8/2001 | Santoianni et al. |
| 6,413,234 B1 | 7/2002 | Thompson et al. |
| 6,440,126 B1 | 8/2002 | Abboud et al. |
| 6,468,260 B1 | 10/2002 | Bumbalough et al. |
| 6,485,455 B1 | 11/2002 | Thompson et al. |
| 6,500,167 B1 | 12/2002 | Webster, Jr. |
| 6,514,249 B1 | 2/2003 | Maguire et al. |
| 6,522,933 B1 | 2/2003 | Nguyen |
| 6,530,897 B1 * | 3/2003 | Nardeo .................. 604/95.04 |
| 6,540,725 B1 | 4/2003 | Ponzi |
| 6,551,271 B1 | 4/2003 | Nguyen |
| 6,562,030 B1 | 5/2003 | Abboud et al. |
| 6,569,158 B1 | 5/2003 | Abboud et al. |
| 6,571,131 B1 | 5/2003 | Nguyen |
| 6,575,933 B1 | 6/2003 | Wittenberger et al. |
| 6,575,966 B1 | 6/2003 | Lane et al. |
| 6,579,287 B1 | 6/2003 | Wittenberger et al. |
| 6,585,717 B1 | 7/2003 | Wittenberger et al. |
| 6,585,718 B1 | 7/2003 | Hayzelden et al. |
| 6,589,234 B1 | 7/2003 | Lalonde et al. |
| 6,592,577 B1 | 7/2003 | Abboud et al. |
| 6,595,988 B1 | 7/2003 | Wittenberger et al. |
| 6,602,247 B1 | 8/2003 | Lalonde |
| 6,602,278 B1 | 8/2003 | Thompson et al. |
| 6,605,086 B1 | 8/2003 | Hayzelden et al. |
| 6,607,505 B1 | 8/2003 | Thompson et al. |
| 6,610,058 B1 | 8/2003 | Flores |
| 6,629,972 B1 | 10/2003 | Lehmann et al. |
| 6,635,053 B1 | 10/2003 | Lalonde et al. |
| 6,648,875 B1 | 11/2003 | Simpson et al. |
| 6,652,506 B1 | 11/2003 | Bowe et al. |
| 6,663,588 B1 | 12/2003 | DuBois et al. |
| 6,733,499 B1 | 5/2004 | Scheib |
| 6,746,445 B1 | 6/2004 | Abboud et al. |
| 6,758,830 B1 | 7/2004 | Schaer et al. |
| 6,758,847 B1 | 7/2004 | Maguire |
| 2001/0021847 A1 | 9/2001 | Abboud et al. |
| 2002/0128639 A1 | 9/2002 | Pless et al. |
| 2003/0018326 A1 | 1/2003 | Abboud et al. |
| 2003/0073992 A1 | 4/2003 | Sliwa, Jr. et al. |
| 2003/0195605 A1 * | 10/2003 | Kovalcheck et al. ........ 607/138 |

* cited by examiner

WIRE REINFORCED ARTICULATION SEGMENT

FIELD OF THE INVENTION

The present invention pertains generally to mechanisms for steering catheters through the vasculature of a patient. More particularly, the present invention pertains to steering mechanisms that rely on a differential bending of separate structures to deflect the distal tip of a catheter for purposes of steering the catheter. The present invention is particularly, but not exclusively, useful as a steering mechanism for a cardiac cryoablation catheter.

BACKGROUND OF THE INVENTION

Steerability, among several attributes, is an important consideration in the manufacture and operation of an invasive catheter. In particular, when the operation of a catheter requires that it be advanced through portions of a patient's vasculature, the ability to steer the catheter along tortuous paths, and into selected branches of the vasculature, is of crucial importance. Further, in addition to having good steering properties, it may also be important to conform the catheter to a particular configuration as it is positioned in the vasculature. In either case, the steering and configuring of an invasive catheter requires that the distal tip of the catheter be articulated in a safe, predictable and controllable manner.

Several devices have been previously suggested for the purpose of steering a catheter through the vasculature of a patient. In the earlier mechanisms, such as the one disclosed in U.S. Pat. No. 1,060,665, that issued to Bell on May 6, 1913, for an invention entitled "Catheter", the steerability of the catheter was provided for by using a pre-bent stiffening member in the catheter's distal end. Subsequently, more complex devices have relied on a pull-wire to deflect the catheter tip. In general, these mechanisms have variously included concentric or eccentric pull-wires that generate an eccentrically applied force on the tip of the catheter. For example, U.S. Pat. No. 4,456,017, which issued to Miles for an invention entitled "Coil Spring Guide with Deflectable Tip" incorporates a concentric core wire for this purpose. On the other hand, U.S. Pat. No. 4,586,923, which issued to Gould et al., uses an eccentric wire for the same purpose. Further, devices have also been proposed which will bias the deflection of a catheter tip in a predetermined plane. An example of such a device is disclosed in U.S. Pat. No. 4,886,067, which issued to Palermo. In the Palermo patent, such a bias is established by flattening the core wire.

Heretofore, as indicated by the examples given above, the steerability of a catheter tip has been primarily engineered by determining the direction in which a deflecting force should be applied to the tip. Accordingly, these earlier devices did not specifically incorporate structural aspects into the construction of a catheter's distal portion with a view toward using this construction as a functional aspect for tip deflection. Such a consideration, however, becomes more significant when, in addition to steerability, the configurability of a catheter in the vasculature of a patient is an important consideration.

In accordance with well known engineering applications, structures will predictably bend according to their shape of the structure and according to particular properties of the material, such as its modulus. By definition, a modulus is the ratio of stress to strain and, for a given material, is constant up to an elastic limit. Importantly, a modulus can be used as a measure of the deflection a material will experience under stress. Also, by definition, stress is the force per unit area acting on a material and tending to change its dimensions, i.e. cause a strain. With this in mind, it is evident to the skilled artisan that when two different materials are subjected to the same force, the materials will experience different strains according to their respective moduli. Further, when two different materials are incorporated into the same structural component of a system, a differential modulus is created for the component by the respective moduli that biases, or favors, a bending of the component according to the dictates of the material having the higher (flexural) modulus.

In light of the above, it is an object of the present invention to provide a device for steering a cardiac cryoablation catheter through the vasculature and in and around the heart of a patient that can be both steered and configured, as desired, while the catheter is in the vasculature and heart of a patient. Another object of the present invention is to provide a device for steering a cardiac cryoablation catheter through the vasculature and heart of a patient that relies on a differential modulus in the structure of the catheter's distal portion to steer and reconfigure the catheter. Still another object of the present invention is to provide a device for steering a cardiac cryoablation catheter through the vasculature and heart of a patient that is relatively easy to manufacture, is simple to use, and is comparatively cost effective.

SUMMARY OF THE PREFERRED EMBODIMENTS

A device for steering a cardiac cryoablation catheter through the vasculature and heart of a patient includes a resilient, cylindrical-shaped articulation segment that is connected to the distal end of a catheter tube. The articulation segment defines a longitudinal axis for the device and, further, the segment is formed with a lumen that extends between its proximal and distal ends. A tip member is affixed to the distal end of the articulation segment, and a flexible spine extends within the lumen between the proximal and distal ends of the segment. Importantly, the flexible spine is off-set from the axis of the articulation segment, and is oriented substantially parallel thereto.

One end of a control wire is attached to the tip member, while the control wire itself extends from the tip member, through the lumen of the articulation segment and through the catheter tube. As intended for the present invention, the control wire is connected to the tip member at an attachment point that lies between the axis of the articulation segment and a location with some opposition to the spine (e.g. diametrically opposite). Further, the device of the present invention includes a mechanism that is engaged with the control wire at the proximal end of the catheter tube for axially pulling on the control wire.

As intended for the present invention, the articulation segment has a first flexural modulus, and the spine has a second flexural modulus. More specifically, for the device of the present invention, the second flexural modulus of the spine is greater than the first flexural modulus of the articulation segment. Consequently, in combination with each other, the spine and the articulation segment establish a differential modulus. Thus, in response to a pulling of the control wire in a proximal direction, the differential modulus allows the tip member to be deflected for the purpose of steering or configuring the catheter in the vasculature and heart of a patient. Additionally, due to the relative location of the spine on the articulation segment, a direction for the deflection of the tip member can be established.

For a specific application of the present invention, the tip member is made of a material having a relatively high thermal conductivity. Additionally, the device produces a fluid which is in a fully saturated liquid state at the operational pressure used for the system. A transfer tube, that extends from the refrigeration source and passes through the catheter tube and through the lumen of the articulation, interconnects the refrigeration source in fluid communication with the tip member. With this connection, the cooled fluid can be released within the tip member during a cardiac cryoablation procedure. The spent refrigerant can then be removed through the lumen of the articulation segment and the catheter tube.

In the manufacture of the device for steering a cardiac cryoablation catheter through the vasculature of a patient, the articulation segment is made with a helical spring which defines the axis and forms the lumen. An inner tube is positioned in the lumen of the helical spring, and an outer tube is positioned against the helical spring opposite the inner tube. The outer tube is then bonded to the inner tube to embed the helical spring therebetween or this whole segment can be made by a continuous or intermittent heat extrusion process. Preferably, both the inner tube and the outer tube can be made of a Pebax material or other suitable material, such as a polyurethane. In any event, the resultant cylindrical-shaped articulation segment will have a first flexural modulus.

Once the articulation segment has been made, the flexible spine is positioned in its lumen and fixedly attached to the articulation segment to extend between its proximal and distal ends. Importantly, as mentioned above, the spine is oriented on the articulation segment off-set from the axis and substantially parallel thereto. As also mentioned above, it is important that the spine have a second flexural modulus that is greater than the first flexural modulus of the articulation segment. In this combination, the tip member is affixed to the distal end of the articulation segment.

A mechanism for controlling the deflection of the tip member is provided by attaching a control wire to the tip member. Specifically, the control wire is attached to the tip member at an attachment point on the tip member. Preferably, the attachment point lies between the axis of the articulation segment and a location in some opposition to the spine (e.g. diametrically opposite), but this need not necessarily be so. In any case, it is the intent of the present invention that, due to the difference in the respective flexural moduli of the articulation segment and the spine, whenever the control wire is pulled, the tip member will predictably bend through an arc in a predetermined plane for the purposes of steering and configuring a catheter in the vasculature and heart of a patient.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
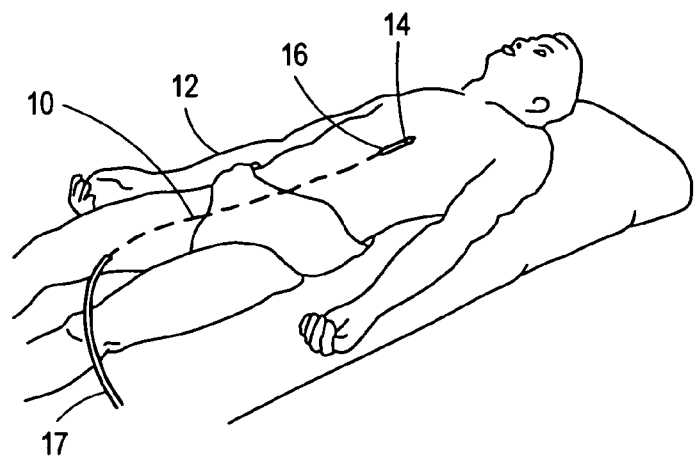
FIG. 1 is a perspective view of a catheter incorporating the device of the present invention, as it is being advanced into the vasculature of a patient for an invasive procedure.

Referring initially to FIG. 1, a cardiac cryoablation catheter (device) in accordance with the present invention is shown and is designated 10. In FIG. 1, the device 10 of the present invention is shown as it is being positioned in the vasculature and into the heart of a patient 12. Importantly, the device 10 includes a tip member 14 that is located at the distal end of the device 10. Further, the device 10 includes an articulation segment 16 that is attached proximal to the tip member 14. Still further, a catheter tube 17 is attached proximal to the articulation segment 16.

Figure 2:
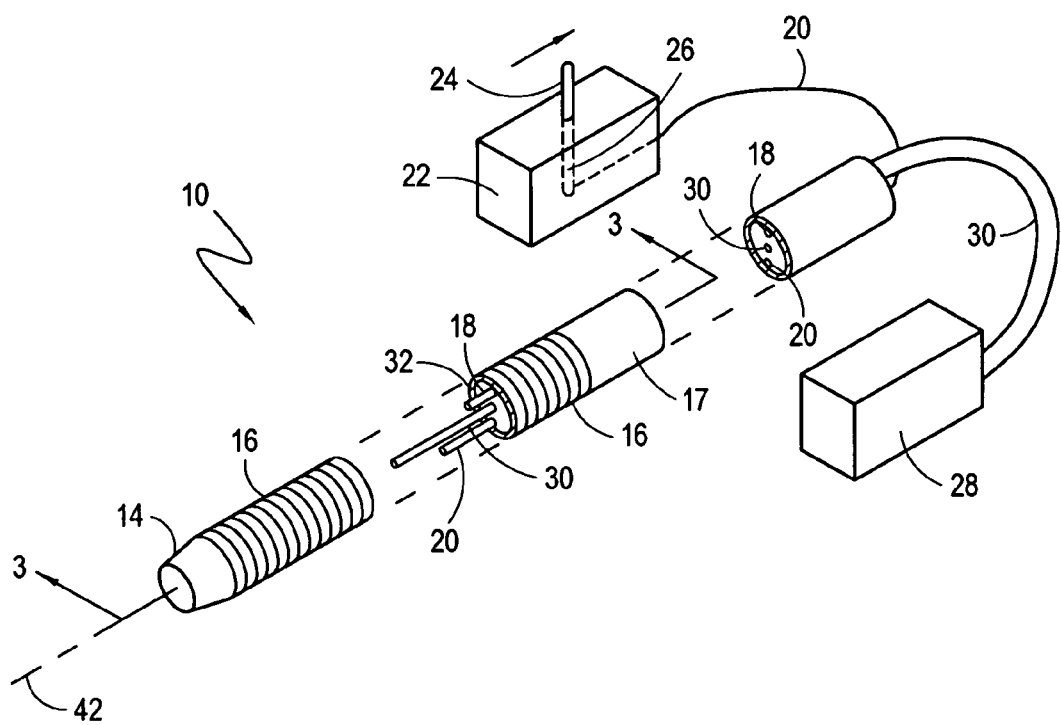
FIG. 2 is a segmented, perspective view of the device of the present invention when it is incorporated into a cardiac cryoablation catheter.

Referring now to FIG. 2, it will be seen that both the articulation segment 16 and the catheter tube 17 are formed with a contiguous lumen 18 that essentially extends through the length of the device 10. Further, FIG. 2 indicates that a control wire 20 extends through the lumen 18 from an extracorporeal control mechanism 22 to the tip member 14. For example, the control mechanism 22 can include a pivot arm 24 which can be rotated about the pivot point 26 by an operator (not shown) to exert a proximally directed force on the control wire 20. It will be appreciated by the skilled artisan, however, that the control mechanism 22 shown in FIG. 2 is only exemplary. Any device known in the pertinent art for generating an axial force on the control wire 20 is suitable for the present invention. Further, it will be appreciated that the control mechanism 22 may be attached directly to the catheter tube 17.

Still referring to FIG. 2, the device 10 is shown to include a refrigeration source 28 which is to be used for the purpose of cooling a fluid. Also shown is a transfer tube 30 that extends from the refrigeration source 28 through the lumen 18 of both the catheter tube 17 and the articulation segment 16. For the device 10, this transfer tube 30 connects the refrigeration source 28 in fluid communication with the tip member 14. Thus, a fluid which is in a fully saturated liquid state at the operational pressure used for the system can be delivered to the tip member 14. Additionally, FIG. 2 shows that, within the articulation segment 16 there is a spine 32 that is positioned between the tip member 14 and the catheter tube 17. The details of the articulation segment 16, and its interactive components, will perhaps be best appreciated with reference to FIG. 3.

Figure 3:
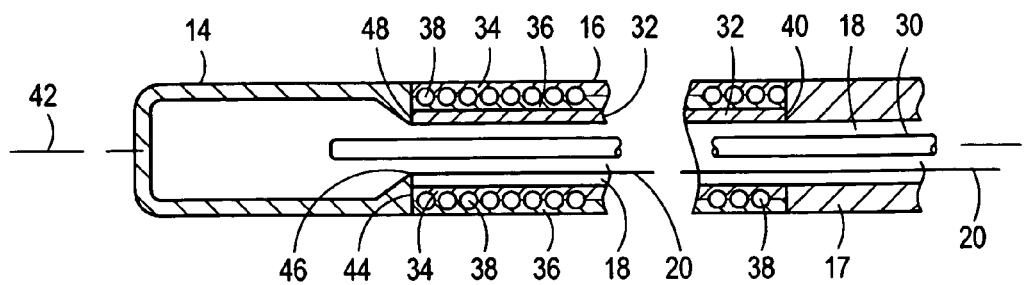
FIG. 3 is a cross sectional view of the segments of the device of the present invention as seen at the distal end portion of a catheter along the line 3—3 in FIG. 2.

In FIG. 3, it can be seen that the articulation segment 16 includes an inner wall 34, an outer wall 36, and a helical spring 38 that is embedded between the inner wall 34 and the outer wall 36. As intended for the present invention, both the inner wall 34 and the outer wall 36 are made of a Pebax material or other suitable material, such as a polyurethane. Thus, the inner wall 34 can be bonded with the outer wall 36 in any manner known in the pertinent art, such as by thermal bonding, or by the use of an appropriate glue or cement or by an extrusion process. In any case, it is important that an effective flexural modulus is established for the articulation segment 16 (i.e. collectively, the walls 34, 36 and the helical spring 38). Importantly, this modulus of the articulation segment 16 must be less than the modulus of the spine 32 when it is positioned within the lumen 18 of the articulation segment 16.

When considered together, because they individually have different moduli, the articulation segment 16 and the spine 32 effectively establish a differential (flexural) modulus for the device 10. With this difference in mind, it should be noted that the articulation segment 16 and the spine 32 are, preferably, co-extensive. Stated differently, they essentially have the same effective length. This is accomplished by having both of the components, articulation segment 16 and spine 32, positioned between the tip member 14 and the distal end of the catheter tube 17. Insofar as the spine 32 is specifically concerned, FIG. 3 shows that the spine 32 is positioned between the tip member 14 and the catheter tube 17 to urge against or is attached to an abutment 40 that is formed as part of the catheter tube 17.

For a discussion of the operation of the device 10 of the present invention, changes in its configuration are perhaps best described relative to the axis 42. More specifically, for this purpose the axis 42 can be generally considered as being the longitudinal axis, or centerline, of the device 10. From this reference, it is then necessary to identify the interactive forces that are involved in the operation of the device 10, and the locations where these forces act on the device 10. This is best accomplished by cross-referencing FIG. 3 with FIG. 4.

Referring first to FIG. 3, it will be seen that the control wire 20 is attached to the base 44 of tip member 14 at an attachment point 46. Also, FIG. 3 shows that the spine 32 is positioned to effectively urge against the tip member 14 at a point 48. Relative to the axis 42, the attachment point 46 is preferably diametrically opposite the point 48, though the points 46 and 48 need not necessarily be at a same radial distance from the axis 42. In fact, as shown in FIG. 4, for purposes of discussion, the attachment point 46 is considered to be at a radial distance "a" from the axis 42, while the point 48 is at a radial distance "d" from the axis 42.

Figure 4:
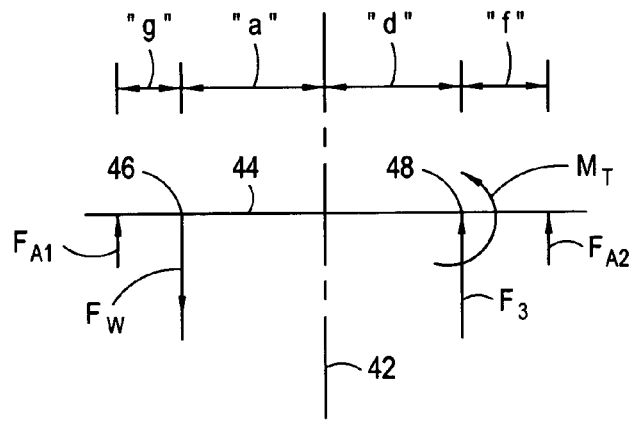
FIG. 4 is a free body diagram of forces acting on the tip member of the device of the present invention as the tip member of the device is being deflected for steerage of the catheter through the vasculature of the patient.

A free body diagram of the forces acting on tip member 14 (represented by its base 44) during an operational deflection of the tip member 14, are shown in FIG. 4. Though only tip member 14 is being specifically considered, it will be appreciated by the skilled artisan that the reaction of the articulation segment 16, and the deflection of the tip member 14 in response to the application of a force, $F_w$, on the tip member 14 by the control wire 20 is the important result.

For the static equilibrium of a body or structure, such as the device 10, it is well known that the summation of forces in all given directions (e.g. an axial direction) must equal zero ($\Sigma F=0$). It is also well known that another condition for static equilibrium is that the summation of moments around a point must equal zero ($\Sigma M=0$). With this in mind, consider the forces acting in an axial direction on the device 10, and the summation of moments about the point 48. For this consideration, the force exerted by the control wire 20 at attachment point 46 is represented by $F_w$, the force exerted by the spine 32 at point 48 is represented by $F_s$, and the resultant forces exerted by the articulation segment 16 on each side of the axis 42 are represented by $F_{A1}$ and $F_{A2}$. For purposes of this discussion, it will be assumed that the transfer tube 30 exerts no effective forces on the base 44. Accordingly:

$$\Sigma F = F_{A1} - F_w + F_s + F_{A2} = 0$$

$$\Sigma M = M_T + (f)F_{A2} + (d+a)F_w - (d+a+g)F_{A1} = 0$$

Figure 5:
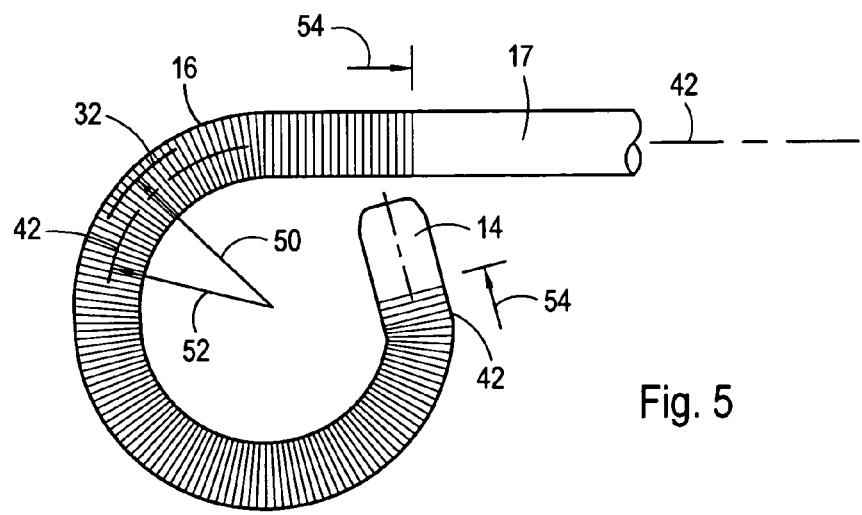
FIG. 5 is a side plan view of the device of the present invention in a fully deflected configuration.

Several observations can be made from the above equations. To do so, however, recall that the moduli for the articulation segment 16 are less than the corresponding moduli for the spine 32. Thus, for a given deflection or compression, $F_s$ will be greater than either $F_{A1}$ or $F_{A2}$ ($F_s > F_{A1} \cong F_{A2}$). Consequently, when a force ($F_w$) is applied at the attachment point 46 by a pull of the control wire 20 in the proximal direction, the spine 32 gives the most resistance. Further, because the force $F_w$ on the control wire 20 is operationally variable, the moment $(d+a)F_w$ can be made greater than the resistive moment $(d+a+g)F_{A1}$. Due to these relationships, the result here is that the articulation segment 16 of the device 10 will deflect in a plane that is generally defined by the spine 32 and the axis 42. More specifically, as best seen in FIG. 5, this deflection will result in a radius of curvature 50 for the spine 32 (only partially shown in FIG. 5) that is greater than a radius of curvature 52 for the axis 42. Further, depending on the magnitude of the force $F_w$ and the resultant movement of the control wire 20, the arc through which the articulation segment is deflected (identified in FIG. 5 by the arrows 54) may be greater than about two radians.

While the particular Wire Reinforced Articulation Segment as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for steering a cardiac cryoablation catheter through the vasculature and heart of a patient which comprises:

a resilient, cylindrical-shaped articulation segment defining a longitudinal axis, said articulation segment having a distal end and a proximal end and forming a lumen therebetween;

a tip member affixed to the distal end of said articulation segment;

a flexible spine fixedly attached to said articulation segment to extend between the proximal and distal ends thereof, and oriented on said articulation segment offset from the axis thereof and substantially parallel thereto;

a control wire having a first end attached to said tip member, wherein the first end of said control wire is attached to said tip member at an attachment point between the axis of the articulation segment and a location opposite to said spine, said control wire being positioned in the lumen of said articulation segment to extend a second end of said control wire from the proximal end of said articulation segment; and a means engaged with the second end of said control wire for axially moving said control wire to selectively deflect said tip member, said articulation segment and said spine through an arc in a plane to steer the catheter.

2. A device as recited in claim 1 wherein said articulation segment has a first flexural modulus, said spine is a wire having a second flexural modulus and, with said second flexural modulus of said spine being greater than said first flexural modulus of said articulation segment to establish a direction for deflection of said tip member.

3. A device as recited in claim 1 wherein said device further comprises a catheter tube having a distal end and a proximal end, and wherein said distal end of said catheter tube is attached to said articulation segment and said proximal end of said catheter tube is attached to said means for moving said control wire.

4. A device as recited in claim 1 wherein said spine and the axis of said articulation segment define a plane, with said spine having a first radius of curvature in the plane during a deflection thereof and the axis having a second radius of curvature in the plane during a deflection of said articulation segment, and wherein the first radius of curvature is greater than the second radius of curvature.

5. A device as recited in claim 1 wherein the arc has an arc length greater than approximately two radians during a deflection of said articulation segment.

6. A device as recited in claim 1 wherein said articulation segment has a length greater than approximately ten millimeters.

7. A device as recited in claim 1 further comprising a pivot arm mounted on said means for moving said control wire, said pivot arm being connected to the second end of said control wire for axially moving said control wire.

8. A device as recited in claim 1 wherein said tip member is made of a thermo-conductive material and said device further comprises:
    a refrigeration source for generating a sub-cooled fluid; and
    a transfer tube extending through the lumen of said articulation segment to interconnect said refrigeration source in fluid communication with said tip member.

9. A device as recited in claim 1 wherein said articulation segment comprises:
    a helical spring defining the lumen;
    an inner tube positioned against said helical spring inside the lumen; and
    an outer tube positioned against said helical spring opposite said inner tube, said outer tube being bonded to said inner tube to embed said helical spring between said inner tube and said outer tube.

10. A device as recited in claim 9 wherein said inner tube and said outer tube are made of a Pebax material.

11. A device for steering a cardiac cryoablation catheter through the vasculature and heart of a patient which comprises:
    a tip member made of a thermo-conductive material;
    a catheter tube having a proximal end and a distal end;
    a first deflection member attached to said tip member and to the distal end of said catheter tube to position said first deflection member therebetween, said first deflection member having a first flexural modulus;
    a second deflection member attached to said tip member and to the distal end of said catheter tube to position said second deflection member substantially parallel to said first deflection member between said tip member and said catheter tube, said second deflection member having a second flexural modulus with the second flexural modulus being greater than the first flexural modulus;
    a control means for pulling said tip member toward said catheter tube to differentially deflect said first deflection member and said second deflection member according to the respective flexural moduli to move said tip member for steering said catheter through the vasculature;
    a refrigeration source for generating a sub-cooled fluid; and
    a transfer tube extending through the lumen of said articulation segment to interconnect said refrigeration source in fluid communication with said tip member.

12. A device as recited in claim 11 wherein said first deflection member is a resilient, cylindrical-shaped articulation segment defining a longitudinal axis, said articulation segment having a distal end and a proximal end and forming a lumen therebetween, and wherein said second deflection member is a flexible spine fixedly attached to said articulation segment to extend between the proximal and distal ends thereof, and oriented on said articulation segment off-set from the axis thereof and substantially parallel thereto.

13. A device as recited in claim 12 wherein the control means includes a control wire attached to said tip member at an attachment point between the axis of the articulation segment and a location diametrically opposite said spine.

14. A device as recited in claim 12 wherein said articulation segment comprises:
    a helical spring defining the lumen;
    an inner tube positioned against said helical spring inside the lumen; and
    an outer tube positioned against said helical spring opposite said inner tube, said outer tube being bonded to said inner tube to embed said helical spring between said inner tube and said outer tube.

15. A method for manufacturing a device for steering a cardiac cryoablation catheter through the vasculature and heart of a patient which comprises the steps of:
    providing a helical spring having a proximal end and a distal end, the helical spring defining an axis and forming a lumen;
    positioning an inner tube in the lumen of the helical spring;
    positioning an outer tube against the helical spring opposite the inner tube;
    bonding the outer tube to the inner tube to embed the helical spring therebetween to create a resilient, cylindrical-shaped articulation segment, with the articulation segment having a first flexural modulus;
    fixedly attaching a flexible spine to said articulation segment to extend between the proximal and distal ends thereof, said spine being oriented on said articulation segment off-set from the axis thereof and substantially parallel thereto, with the spine having a second flexural modulus wherein the second flexural modulus is greater than the first flexural modulus;
    affixing a tip member to the distal end of the articulation segment; and
    attaching a control wire to the tip member to differentially deflect the articulation segment and the spine according to their respective flexural moduli, whenever the control wire is pulled, to move the tip member for steering the catheter through the vasculature.

16. A method as recited in claim 15 wherein the control wire is attached to the tip member at an attachment point between the axis of the articulation segment and a location diametrically opposite the spine.

17. A method as recited in claim 15 wherein the inner tube and the outer tube are made of a Pebax material.

18. A method as recited in claim 15 wherein the tip member is made of a thermo-conductive material and the method further comprises the step of connecting a refrigeration source in fluid communication with the tip member, wherein the refrigeration source is used for generating a sub-cooled fluid.

* * * * *